United States Patent [19]

Miura et al.

[11] Patent Number: 5,625,095
[45] Date of Patent: Apr. 29, 1997

[54] PROCESS FOR PRODUCING HIGH PURITY ACETIC ACID

[75] Inventors: Hiroyuki Miura; Masahiko Shimizu, both of Hyogo; Takashi Sato, Hiroshima; Yoshiaki Morimoto, Niigata; Masahiro Kagotani, Hyogo, all of Japan

[73] Assignee: Daicel Chemical Industries, Ltd., Osaka, Japan

[21] Appl. No.: 458,348

[22] Filed: Jun. 2, 1995

[30] Foreign Application Priority Data

| Jun. 15, 1994 | [JP] | Japan | 6-132724 |
| Jun. 20, 1994 | [JP] | Japan | 6-137213 |
| Jun. 30, 1994 | [JP] | Japan | 6-149652 |
| Jul. 6, 1994 | [JP] | Japan | 6-154401 |
| Aug. 22, 1994 | [JP] | Japan | 6-196524 |

[51] Int. Cl.$^6$ .................................................. C07C 51/12
[52] U.S. Cl. .................................................. 562/519; 562/608
[58] Field of Search .................................................. 562/519, 608

[56] References Cited

U.S. PATENT DOCUMENTS

| 4,008,131 | 2/1977 | Price. |
| 4,615,806 | 10/1986 | Hilton. |
| 5,001,259 | 3/1991 | Smith et al. . |
| 5,155,265 | 10/1992 | Scates et al. . |
| 5,214,203 | 5/1993 | Koyama et al. . |
| 5,371,286 | 12/1994 | Blay et al. ............................... 562/519 |

FOREIGN PATENT DOCUMENTS

| 0265140 | 4/1988 | European Pat. Off. . |
| 487284 | 11/1991 | European Pat. Off. . |
| 0497521 | 8/1992 | European Pat. Off. . |
| 0638538 | 2/1995 | European Pat. Off. . |
| 1063133 | 3/1967 | United Kingdom . |

*Primary Examiner*—Gary Geist
*Assistant Examiner*—Rosalynd Williams
*Attorney, Agent, or Firm*—Flynn, Thiel, Boutell & Tanis, P.C.

[57] ABSTRACT

A high purity acetic acid is prepared by reacting methanol with carbon monoxide in the presence of a rhodium catalyst, iodide salts, and methyl iodide, wherein an acetaldehyde concentration in the reaction liquid is maintained at 400 ppm or lower. This may be attained by contacting the liquid containing carbonyl impurities with water to separate and remove the carbonyl impurities. After that, the liquid can be returned to the reactor.

2 Claims, 1 Drawing Sheet

FIG. 1

FIG. 2

PROCESS FOR PRODUCING HIGH PURITY ACETIC ACID

FIELD OF THE INVENTION

The present invention relates to a novel process for producing high purity acetic acid formed by carbonylating methanol in the presence of a rhodium catalyst. More specifically, the present invention relates to a novel process for producing high purity acetic acid, wherein organic iodides and carbonyl impurities contained in acetic acid formed by rhodium-catalyzed carbonylation are reduced.

DESCRIPTION OF THE RELATED ART

Various processes are known as an industrial process for producing acetic acid. Among them, a process for producing acetic acid by continuously reacting methanol with carbon monoxide in the presence of water using a rhodium catalyst and methyl iodide is the best process.

Recently, reaction conditions and catalyst improvement have been investigated, and processes for industrially producing acetic acid at a high productivity are disclosed, wherein catalyst stabilizers such as iodide salts are added and the reaction is carried out at a lower water content than conventional (U.S. Pat. No. 5214203 and U.S. Pat. No. 5001259). It is disclosed therein that the water content in a reaction liquid is reduced to decrease by-products such as carbon dioxide and propionic acid. However, there is the problem that other trace impurities increase in amount as the productivity of acetic acid increases and deteriorate the quality of product acetic acid. In particular, in a quality test by which the amounts of very minute reducing impurities present in acetic acid are checked, which is called a permanganate reducing substance test (permanganate time), minute increase in impurities having minute concentrations, which are hard to quantitatively determine, even with high-grade instrumental analysis, can be detected, and these impurities lead to deterioration of product quality.

Impurities which particularly exert influences on different kinds of applications are contained as well in these trace impurities. For example, it is known that in a process for producing vinyl acetate from ethylene and acetic acid, the impurities deteriorate a palladium series catalyst used in the process. These impurities include carbonyl compounds and organic iodides. To be specific, it is known that they include carbonyl compounds such as acetaldehyde, butylaldehyde, crotonaldehyde, and 2-ethylcrotonaldehyde, aldol condensation products thereof, and alkyl iodides such as ethyl iodide, butyl iodide, and hexyl iodide (EP-A 487284).

However, these carbonyl impurities which deteriorate permanganate time have boiling points tightly close to those of iodide catalyst accelerators, and it is difficult to sufficiently remove alkyl iodides which deactivate catalysts for producing vinyl acetate by ordinary means such as, for example, distillation.

In view of the forgoing, there are disclosed conventional techniques such as the treatment of crude acetic acid containing these minute reducing impurities with ozone and oxidizing agents. However, treatment with ozone and oxidizing agents have limits in the concentrations of the impurities to be treated. For example, compounds generated by decomposing unsaturated compounds such as crotonaldehyde and 2-ethylcrotoaldehyde by ozone processing are saturated aldehydes. Aldehydes themselves have reducing properties and are nothing but compounds which deteriorate the permanganate time. Accordingly, refining such as distillation and treatment with active carbon is required after treatment with ozone in order to remove saturated aldehydes (U.S. Pat. No. 5155265).

It is known as well to treat crude acetic acid with macro reticulated strong acid cation exchange resins, or strongly acidic cation exchange resins, substituted with silver to remove organic iodides (U.S. Pat. No. 4615806). While this method is effective for removing alkyl iodides, hydrogen iodide, and inorganic iodide salts, it is insufficient for removing the unsaturated carbonyl impurities described above.

While in every method described above, crude acetic acid is processed, it is attempted as well to remove carbonyl impurities contained in a process circulating liquid in a continuous reaction process. That is, a method for removing carbonyl impurities is disclosed, wherein a methyl iodide recirculating stream to a carbonylation reactor is reacted with amino compounds which react with carbonyl impurities to form water soluble nitrogen-containing derivatives, and an organic methyl iodide phase is then separated from an aqueous derivative phase, followed by distilling the methyl iodide phase to remove carbonyl impurities (EP-A 487284). However, the concentration of the carbonyl impurities contained in an organic stream recirculated into the carbonylation reactor described above is still high, and therefore it is not clear if the carbonyl impurities have been sufficiently removed. Further, a new problem of removing nitrogen-containing compounds is involved.

BRIEF DESCRIPTION OF THE DRAWINGS

In the drawings.

10: Carbonylation reactor.
12: Flasher.
14: Methyl iodide—acetic acid splitter column.
30: Lower phase in liquid separator.
40, 60: Distillation columns.

SUMMARY OF THE INVENTION

An object of the present invention is to provide a process for producing high purity acetic acid, wherein carbonyl compounds or organic iodides which are impurities of acetic acid as described above are reduced by controlling conditions of a reactor in which they are generated.

Further, an object of the present invention is to provide an effectual, specific means to carry out such control.

The present inventors have noted that a great part of the impurities described above originate in acetaldehyde generated during the reaction and that these impurities are formed in the reactor. That results a finding that both carbonyl compounds and organic iodides, which are impurities contained in the resulting acetic acid, can be reduced by controlling the acetaldehyde concentration in a reactor to thereby obtain high purity acetic acid, thus completing the present invention.

The invention provides a process for producing a high purity acetic acid, comprising the steps of continuously reacting methanol with carbon monoxide in the presence of a rhodium catalyst, an iodide salt, and methyl iodide, wherein the reaction is carried out while maintaining an acetaldehyde's concentration in the reaction liquid at 400 ppm or lower.

It is preferable that the above defined reaction is carried out by removing acetaldehyde from the process liquid being circulated into a reactor to maintain the acetaldehyde concentration in the reaction liquid at 400 ppm or lower.

The invention moreover provides a process for producing a high purity acetic acid comprising the steps of reacting methanol with carbon monoxide in the presence of a rhodium catalyst, an iodide salt and methyl iodide, separating the resulting reaction liquid into a volatile phase containing acetic acid, methyl acetate and methyl iodide and a low volatile phase containing the rhodium catalyst, distilling the volatile phase to obtain a product mixture containing acetic acid and the overhead containing methyl acetate and methyl iodide, and recirculating said overhead into the reactor, wherein the overhead or a condensate of the carbonyl impurities of said overhead is contacted with water to separate it into an organic phase containing methyl acetate and methyl iodide and an aqueous phase containing the carbonyl impurities containing acetaldehyde, and said organic phase is recirculated into the reactor.

The invention, in addition, provides a process for producing a high purity acetic acid comprising the steps of reacting methanol with carbon monoxide in the presence of a rhodium catalyst, an iodide salt and methyl iodide, separating the resulting reaction liquid into a volatile phase containing acetic acid, methyl acetate and methyl iodide and a low volatile phase containing the rhodium catalyst, distilling the volatile phase to obtain a product mixture containing acetic acid and the overhead containing methyl acetate and methyl iodide, and recirculating said overhead into the reactor, wherein the overhead containing acetaldehyde and methyl iodide is distilled at a top temperature of 55° C. or higher, at a reflux tank's temperature of 25° C. or higher, at a pressure of 1 kg/cm$^2$ or more, and acetaldehyde is separated and removed to be recirculated into the reactor.

The invention besides provides a process for producing high purity acetic acid comprising the steps of reacting methanol with carbon monoxide in the presence of a rhodium catalyst, an iodide salt and methyl iodide, separating the resulting reaction liquid into a volatile phase containing acetic acid, methyl acetate and methyl iodide and a low volatile phase containing the rhodium catalyst, distilling the volatile phase to obtain a product mixture containing acetic acid and an overhead containing methyl acetate and methyl iodide, and recirculating said overhead into the reactor, wherein the overhead containing acetaldehyde and methyl iodide is distilled at a top temperature of less than 55° C. and a reflux tank's temperature of less than 25° C. in the presence of an alcohol and acetaldehyde is separated and removed to be recirculated into the reactor. It is preferable that methanol is introduced at a lower position than a stage charged with the overhead containing acetaldehyde and methyl iodide.

A preferable embodiment of the invention is to maintain an acetaldehyde's concentration in the reaction liquid at 400 ppm or lower by separating the resulting reaction liquid into a volatile phase containing acetic acid, methyl acetate and methyl iodide and a low volatile phase containing the rhodium catalyst, distilling the volatile phase to obtain a product mixture containing acetic acid and the overhead containing methyl acetate and methyl iodide, and recirculating said overhead into the reactor, wherein the overhead or a condensate of the carbonyl impurities of said overhead is contacted with water to separate it into an organic phase containing methyl acetate and methyl iodide and an aqueous phase containing the carbonyl impurities containing acetaldehyde, and said organic phase is recirculated into the reactor.

Another preferable embodiment of the invention removes acetaldehyde and methyl iodide by the overhead containing acetaldehyde and methyl iodide being distilled at a top temperature of 55° C. or higher, at a reflux tank's temperature of 25° C. or higher, at a pressure of 1 kg/cm$^2$ or more, and acetaldehyde is separated and removed to be recirculated into the reactor. Alternatively, the overhead containing acetaldehyde and methyl iodide is distilled at a top temperature of less than 55° C. and a reflux tank's temperature of less than 25° C. in the presence of an alcohol and acetaldehyde is separated and removed to be recirculated into the reactor.

As shown above, the overhead is distilled under specified conditions to separate and remove acetaldehyde, and thereafter recirculated into the reactor.

The term, the low volatile, includes non-volatile.

First, the process for producing acetic acid according to the present invention will be explained.

The rhodium catalyst used in the present invention is present in a reaction liquid in the form of a rhodium complex. Accordingly, the rhodium catalyst may be used in any form as long as it is changed to a complex which dissolves in the reaction liquid. To be specific, rhodium iodine complexes and rhodium carbonyl complexes such as $RhI_3$ and $[Rh(CO)_2I_2]^-$ are effectively used. The amount used is from 200 to 1,000 ppm, preferably 300 to 600 ppm in terms of concentration in the reaction liquid.

In the present invention, an iodide salt is added particularly for stabilizing the rhodium catalyst under low water content and suppressing side reactions. This iodide salt may be any one as long as it generates an iodine ion in a reaction liquid. The examples thereof include alkaline metal iodide salts such as LiI, NaI, KI, RbI, and CsI, alkaline earth metal iodide salts such as $BeI_2$, $MgI_2$, and $CaI_2$, and aluminum group metal iodide salts such as $BI_3$ and $AlI_3$. Organic iodide salts can be used besides the metal iodide salts and include, for example, quaternary phosphonium iodide salts (methyl iodide adducts or hydrogen iodide adducts of tributyl phosphine and triphenyl phosphine), and quaternary ammonium iodide salts (methyl iodide adducts or hydrogen iodide adducts of tertiary amine, pyridines, imidazoles, and imides). In particular, the alkaline metal iodide salts such as LiI are preferred. The use amount of the iodide salts is 0.07 to 2.5 mole/liter, preferably 0.25 to 1.5 mole/liter in terms of iodide ion in a reaction liquid.

In the present invention, methyl iodide is used as a catalyst accelerator and caused to be present in a reaction liquid in an amount of 5 to 20 weight %, preferably 12 to 16 weight %.

A water content in a reaction liquid in the present invention is 15 weight % or less, preferably 10 weight % or less, and more preferably 1 to 5 weight %.

As the reaction in the present invention is a continuous reaction, methyl acetate formed by reacting raw material methanol with acetic acid is present in 0.1 to 30 weight %, preferably 0.5 to 5 weight %, and the balance of principal components in the reaction liquid is acetic acid which is a product as well as a reaction solvent.

In the present invention, the typical temperature in the carbonylation of methanol is about 150° to 250° C., and temperature ranges of about 180° to 220° C. are preferred. A partial pressure of carbon monoxide can be changed in a wide range and is typically about 2 to 30 atm, preferably 4 to 15 atm. The whole reactor pressure resides within a range of about 15 to 40 atm because of the partial pressures of the by-products and the vapor pressure of liquid contained therein.

The process of the present invention will be explained below based on a drawing.

Figure 1:
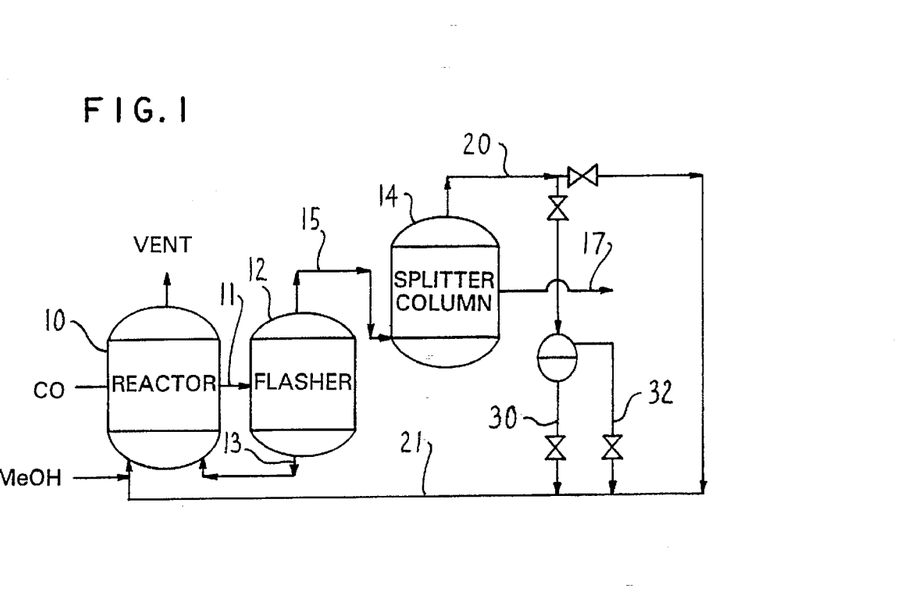
FIG. 1 shows a flow diagram of a reaction used for the carbonylation of methanol to acetic acid-acetic acid recovery system.

FIG. 1 is a flow diagram showing a reaction—acetic acetic acid recovery system used for rhodium-catalyzed carbonylation of methanol to acetic acid.

The reaction from methanol to acetic acid—acetic acid recovery system shown in FIG. 1 includes a carbonylation reactor 10, a flasher 12, and a methyl iodide—acetic acid splitter column 14. Usually, reaction liquid contents are automatically maintained at a fixed level in the carbonylation reactor 10. Fresh methanol and a sufficient amount of water are continuously introduced into this reactor according to necessity, and at least a measurable concentration of water is maintained in a reaction solvent. An alternative distillation system can also be used as long as it is equipped with means for recovering crude acetic acid, and means for recirculating a catalyst liquid, methyl iodide, and methyl acetate into the reactor.

In a preferred process, carbon monoxide is continuously introduced into an immediate lower part of a stirrer used for stirring contents in the carbonylation reactor 10. A gaseous supplying material is dispersed all over the reaction liquid. A gaseous purge stream is discharged from the reactor to prevent the accumulation of gaseous by-products and maintain a set partial pressure of carbon monoxide in the whole fixed reactor pressure. The reactor temperature is automatically controlled, and a carbon nonoxide-supplying material is introduced at a reaction rate sufficient for maintaining the preferred reactor pressure. Liquid products are withdrawn from the carbonylation reactor 10 at a speed sufficient for maintaining a fixed level and introduced at an intermediate point between the top and bottom of the flasher 12 via a line 11.

A catalyst liquid is withdrawn from the flasher 12 as a bottom stream 13 (acetic acid containing mainly the rhodium catalyst and iodide salts together with small amounts of methyl acetate, methyl iodide, and water) and returned to the carbonylation reactor 10. An overhead 15 from the flasher 12 contains mainly product acetic acid together with methyl iodide, methyl acetate, and water.

Product acetic acid (can be withdrawn as a bottom stream) withdrawn as a side stream close to the bottom of the methyl iodide—acetic acid splitter column 14 is further refined by methods known by persons having ordinary skill in the art. An overhead 20 from the methyl iodide—acetic acid splitter column 14 containing mainly methyl iodide and methyl acetate as well as small amounts of water and acetic acid is recirculated into the carbonylation reactor 10 via a line 21. The overhead 20 is typically separated into two liquid phases by condensing when a sufficient amount of water is present. A lower phase 30 comprises mainly methyl iodide and small amounts of methyl acetate and acetic acid, and an upper phase 32 comprises mainly water, acetic acid, and a small amount of methyl acetate.

In the present invention, it is important in the reaction—acetic acid recovery system to carry out the reaction while keeping an acetaldehyde concentration in the reaction liquid at 400 ppm or less. An acetaldehyde concentration exceeding 400 ppm is not preferred because impurity concentrations in acetic acid, which is a product, increase, and a complicated refining processing step is required. A method in which reaction conditions are managed and a method in which acctaldehyde is removed from a process liquid circulated into a reactor are available in order to maintain the acetaldehyde concentration in the reaction liquid at 400 ppm or less.

The management of the reaction conditions includes increasing the hydrogen partial pressure, water concentration, and rhodium catalyst concentration. These operations mainly lower the acetaldehyde concentration in the reaction liquid in the carbonylation reactor 10, which results in controlling an aldol condensation of acetaldehyde and decreasing by-production speeds of reducing substances such as crotonaldehyde and 2-ethylcrotonaldehyde, and alkyl iodides such as hexyl iodide. However, in some cases, these methods have a defect of increasing a by-production speed of propionic acid.

In view of the forgoing, in order to control the acetaldehyde concentration in the reaction liquid in the carbonylation reactor to 10 to 400 ppm or less, it is prefertable to remove acetaldehyde from the process liquid circulated into the carbonylation reactor 10.

The method in which acetaldehyde is removed and the method in which the reaction conditions are controlled can be used in combination.

Hydrogen partial pressure in the carbonylation reactor 10 originates in hydrogen generated in the system by aqueous gas shift reaction in the present reaction and, in some cases, originates in hydrogen introduced into the reactor together with raw material carbon monoxide.

A method for removing acetaldehyde from the process liquid circulated into the carbonylation reactor 10 includes methods such as distillation and extraction, or the combination thereof, and distillation/extraction.

Preferred as the process liquid, which is a target for removing carbonyl impurities containing acetaldehyde, are the upper phase 32 of the condensate of the overhead 20, the lower phase 30, which is rich in methyl iodide, a homogeneous liquid of the overhead 20, if the overhead 20, is not separated into two layers, an absorbing liquid for vent gas in a waste gas absorbing system, and a low boiling liquid obtained by further distilling crude acetic acid liquid withdrawn from the line 17 close to the bottom of the splitter column 14, because the concentrations of acetaldehyde are high. Of them, most preferred is the upper phase 32, the lower phase 30, the homogeneous liquid of the overhead 20, if the overhead 20 is not separated into two layers, or the carbonyl impurities concentrate thereof. Crude acetic acid liquid withdrawn from the line 17 is usually turned to product acetic acid after the crude acetic acid liquid is dehydrated in the subsequent distillation column and then introduced into an acetic acid product column for distilling to separate high boiling and low boiling matters.

The process liquid which is a target for removing carbonyl impurities containing acetaldehyde as described above usually contains methyl iodide of 5 to 90 weight %, acetaldehyde 0.05 to 50 weight %, methyl acetate of 0 to 15 weight %, acetic acid of 0 to 80 weight %, moisture of 0.1 to 40 weight %, and other carbonyl impurities.

The process liquid containing acetaldehyde and others contains useful components such as methyl iodide, methyl acetate and the like and therefore is circulated to the carbonylation reactor 10 for reuse. Accordingly, the acetaldehyde concentration in the reactor can be reduced by separating and removing acetaldehyde from these circulating liquids.

A method for separating carbonyl impurities containing acetaldehyde includes a method in which a process liquid containing acetaldehyde is distilled and separated in one distillation column, a method in which low boiling components comprising acetaldehyde and methyl iodide are first separated from other components by distillation, and then acetaldehyde is Further separated from methyl iodide by distillation, and a method in which utilizing a property that acetaldehyde is well miscible with water and methyl iodide is scarcely miscible with water, extraction with water is employed for separating methyl iodide from acetaldehyde.

When acetaldehyde is separated directly from the process liquid in a single distillation column, it is pretty difficult to concentrate acetaldehyde because the boiling point of methyl iodide is close to that of acetaldehyde. The concentration of acetaldehyde by distillation in a nonaqueous system such as methyl iodide not only generates paraldehyde and metaldehyde and prevents acetaldehyde from concentrating but also deposites metaldehyde in the process and prevents stable operation. In view of the foregoing, the method in which extraction with water is used for separating methyl iodide from acetaldehyde is preferred, and particularly preferred is a method in which, after an acetaldehyde liquid containing methyl iodide is separated from a process liquid by distillation, acetaldehyde is selectively extracted with water, and this is further separated from a distillation/separation process. According to this method, acetaldehyde can be very efficiently concentrated and removed because the distillation temperature is high in the concentration of a water extract by distillation, and an increase in hydrogen ion concentration in a distillate due to the decomposition of ester can suppress the generation of paraldehyde and metaldehyde. When distillation for separation is carried out in one distillation column, water may be charged into the distillation column, and/or the distillation temperature and pressure may be elevated to control the generation of paraldehyde and metaldehyde. Further, distillation conditions may be varied to positively generate paraldehyde and metaldehyde, and acetaldehyde may be separated and removed from the bottom products in the forms of paraldehyde and metaldehyde. In this case, solvents dissolving metaldehyde, such as methanol, have to be charged into the column to prevent clogging caused by the crystallization of metaldehyde.

The method in which extraction with water is used For separating methyl iodide from acetaldehyde will be explained below in detail.

In this water extraction method, carbonyl impurities contained in the lower phase 30 in a liquid separator containing carbonyl compounds such as, for example, acetaldehyde, crotonaldehyde, and butylaldehyde are separated from a reaction product by extracting them with water to form a recirculating stream containing no carbonyl impurities. According to a preferred embodiment, the lower phase 30 in the liquid separator bath is separated into an organic phase recirculating stream containing methyl iodide and an aqueous phase stream containing carbonyl impurities, particularly acetaldehyde by extraction with water, and carbonyl impurities are then removed From the organic phase recirculating stream to the reactor.

At the first step in the preferred method, the lower phase 30 in the liquid separator bath containing carbonyl impurities such as, for example, acetaldehyde, crotonaldehyde and butylaldehyde is contacted to water to extract the carbonyl impurities into an aqueous phase. The carbonyl impurities can be determined by an analysis before processing. The extraction is carried out at temperatures of 0 to 100° C. for 1 second to 1 hour. Any pressure can be employed. Pressure is not essential in this method, and advantageous conditions can be selected in terms of cost. There can be used as an extractor, every suitable apparatus which is known in terms of technique, such as a combination of mixers and settlers, the combination of static mixers and decanters, RDC (rotated disk contactor), a Karr column, a spray column, a packed column, a perforated plate column, a baffle column, and a pulsation column.

After passing through an extractor to a decanter, the aqueous phase stream containing carbonyl impurities and the organic phase stream containing no carbonyl impurities are obtained. The organic phase stream is recirculated to the carbonylation reactor. The aqueous phase stream is sent to a distillation column to separate the carbonyl impurities from water, and water is recirculated to the extractor. The value of the carbonyl impurities removed can be determined by an analysis method.

Next, the distilling method under particular conditions for separating methyl iodide and acetaldehyde is detailed.

Investigations intensively made by the present inventors have resulted in finding that the generation and deposition of paraldehyde and metaldehyde which are the condensation products of acetaldehyde can be controlled, and methyl iodide can efficiently be separated from acetaldehyde by controlling top temperature, reflux tank temperature, and pressure or controlling top temperature and reflux tank temperature in the presence of alcohol in distilling a mixed liquid containing acetaldehyde and methyl iodide, and completing the present invention.

That is, the present invention provides a process for efficiently separating acetaldehyde and methyl iodide by distilling a mixed liquid containing acetaldehyde and methyl iodide, for example the overhead described above, at top temperatures of 55° C. or higher, reflux tank temperatures of 25° C. or higher, and pressures of 1 $kg/cm^2$ or more, or distilling it at top temperatures of less than 55° C. and circulating tank temperatures of less than 25° C. in the presence of alcohol.

Figure 2:
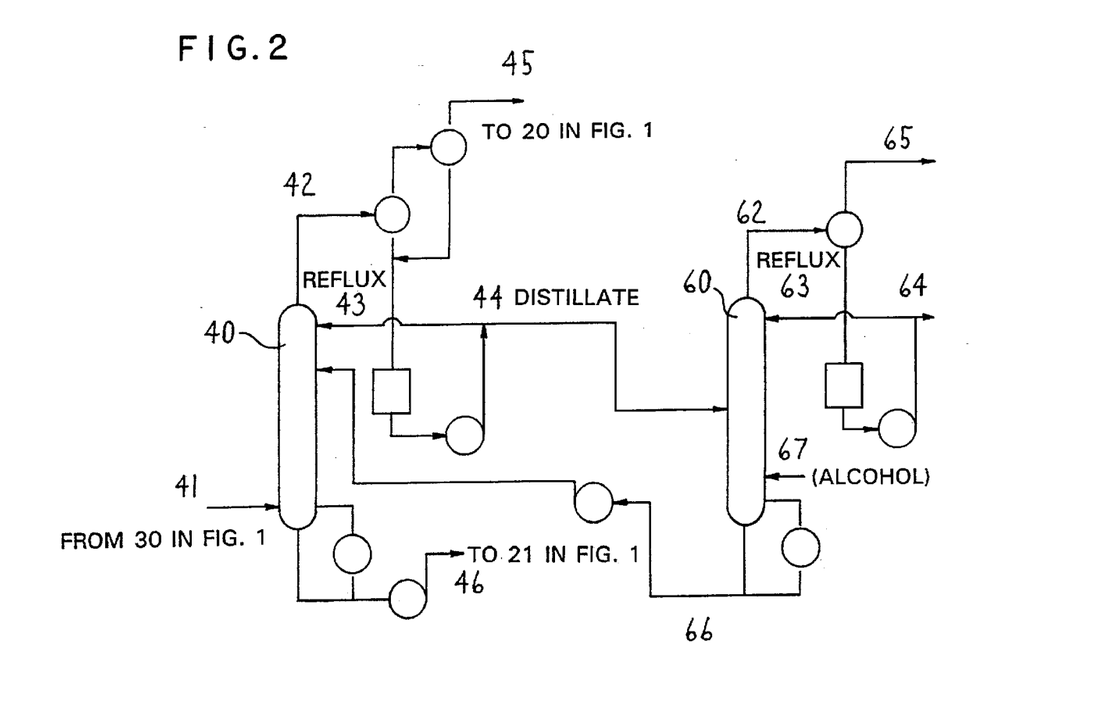
FIG. 2 shows one example of a distillation system for separating methyl iodide from acetaldehyde.

Followings, FIG. 1 and FIG. 2 are used to illustrate.

A recirculating stream 21 can be formed by the lower phase 30, the upper phase 32 or, if they are not separated, the whole overhead 20, or combining these phases and overhead withdrawn from the methyl iodide—acetic acid splitter column 14 with other recirculated products containing methyl iodide, methyl acetate, water, and impurities.

The lower phase 30, the upper phase 32 or the whole overhead 20 withdrawn from the methyl iodide—acetic acid splitter column 14, or the recirculating stream 21 is introduced into a distillation column 40 and subjected to the processing of the present invention. Every suitable equipment which is known in terms of techniques can be used for distillation columns and separation. The number of stages distillation columns may be any number. Two or more distillation columns may be used to carry out the processing of the present invention if it can not be carried out in a single distillation column for reasons of facilities cost.

The case where the processing of the present invention is carried out in the two distillation column will be explained below referring to FIG. 2.

The lower phase 30, the upper phase 32 or the whole overhead 20 withdrawn from the methyl iodide—acetic acid splitter column 14, or the recirculating stream 21 is introduced into the distillation column 40, and a methyl iodide recirculating stream withdrawn from the bottom of the column is recirculated into the reactor via a line 46. A distillate 44 is obtained from the top.

The distillate 44 from the distillation column 40 is introduced into a distillation column 60 and subjected to the processing of the present invention. A methyl iodide recirculating stream from which most of acetaldehyde has been removed is recirculated into the upper part of the distillation column 40 via a line 66. Or, in the case where a liquid from which most of the acetaldehyde has been removed and which is rich in methyl iodide is obtained from the top, a top distillate is recirculated into the distillation column 40.

Usually, the process liquid of the whole overhead withdrawn from the methyl iodide—acetic acid splitter column 14 contains methyl iodide of 5 to 90 weight %, acetaldehyde of 0.05 to 50 weight %, methyl acetate of 0 to 15 weight %, acetic acid of 0 to 80 weight %, moisture of 0.1 to 40 weight %, and other carbonyl impurities.

Because the process liquid containing acetaldehyde described above contains useful components such as methyl iodide and methyl acetate, it is circulated into the carbonylation reactor 10 for reuse. Accordingly, after separating and removing acetaldehyde as much as possible from these process liquids, they are preferably circulated into the reactor.

If acetaldehyde is not sufficiently removed, acetaldehyde accumulates in the process liquid, and the aldol condensation of acetaldehyde is promoted, which result in accelerating the by-production speeds of reductive substances such as crotonaldehyde and 2-ethylcrotonaldehyde and alkyl iodides such as hexyl iodide and therefore lead to obtaining product acetic acid containing these impurities in a large amount.

The separation of acetaldehyde and methyl iodide is difficult because the boiling points of acetaldehyde and methyl iodide are close to each other, and in addition, the concentration of methyl iodide by distillation in a nonaqueous system not only generates paraldehyde and metaldehyde and prevents acetaldehyde from concentrating but also deposits metaldehyde in the process and prevents stable operation.

Paraldehyde is a trimer of acetaldehyde and is a liquid having a boiling point of 124° C. and a melting point of 10° C. In general, paraldehyde is liable to be generated from acetaldehyde at low temperatures of 0 to −10° C., and critical generation temperature is 55° C. It was confirmed in a laboratory that paraldehyde was generated at 20° C.

Metaldehyde is a tetramer through a hexamer of acetaldehyde and is a white acicular crystal having melting points of 140° to 246° C. Metaldehyde is formed at lower temperature than paraldehyde and is generally generated at a degree of −10° to −40° C. It was confirmed in a laboratory that metaldehyde was generated at a degree of 5° C. a temperature of −40° C. or less causes polymerization. Paraldehyde and metaldehyde have stereoisomers, and it was confirmed that they had different melting point and solubility to solvents.

As shown here, the generation of paraldehyde and metaldehyde is influenced by temperature. That is, controlling the operation pressure and operation temperature in a distillation column has made it possible to separate and remove acetaldehyde.

That is, it has been found that distilling at top temperatures of 5° C. or higher, reflux tank temperatures of 25° C. or higher, and a pressure of 1 kg/cm² or more in a distillation column can control the generation of paraldehyde and metaldehyde and improves the separation efficiency of methyl iodide from acetaldehyde. Further, shortening the residence time for returning to the distillation column from a top condenser through a reflux tank is effective as well for suppressing the generation of paraldehyde and metaldehyde.

Further, it has been found that since distilling at top temperatures of less than 55° C. and reflux tank temperatures of less than 25° C. converts acetaldehyde to paraldehyde and metaldehyde at the top, which have higher boiling points and therefore are moved to the bottom, acetaldehyde can be removed from bottom products in the form of paraldehyde and metaldehyde. However, because metaldehyde is a solid having a low solubility, particularly to methyl iodide, and is deposited, it clogs not only the perforated plates and packing of the distillation column but also respective nozzles, pipelines and valves and hinders operation. The present inventors have found that metaldehyde is dissolved in alcohols such as methanol, ethanol, and propanol. That is, distillation in the presence of alcohols has made it possible to prevent clogging.

There may be used any alcohols in the present invention including aliphatic alcohols such as methanol, ethanol, and propanol, aromatic alcohols such as benzyl alcohol, and polyhydric alcohols such as ethylene glycol. Methanol which is also used as a raw material is preferred.

Detailed investigations on the solubility of metaldehyde have resulted in finding that solubilities increase in the order of methyl iodide<<acetaldehyde=methanol<mixed solution of methyl iodide and methanol and that the optimum point of solubility is present in the mixed solution of methyl iodide and methanol. It has been confirmed that in the composition of bottom products from the distillation column in the continuous production process for acetic acid, the recrystallization temperature is 18° C. at a methyl iodide/methanol weight ratio of 3/1, 12° C. at 5/4, 6° C. at 3/4, and −9° C. or lower at 1/2. The preferred methyl iodide/methanol weight ratio, which depends on a thermal insulation state, is 5/4 to 1/2.

A charging position for alcohol can be a charging stage which can be separated so that alcohol is not lost from the top. It is preferably a lower part than a charging stage for a mixed solution of acetaldehyde and methyl iodide, which is subjected to the processing of the present invention.

The generation and decomposition of paraldehyde and metaldehyde seem to be influenced by the strength of coexisting acids as well as temperature and time.

In the present invention, the amount of acetaldehyde to be removed is an amount by which an acetaldehyde concentration in a reaction liquid during a steady continuous reaction can be maintained at 400 ppm or less (preferably 350 ppm or less, more preferably 300 ppm or less). Essentially, it is the whole amount of acetaldehyde generated under steady continuous reaction conditions, that is, an amount almost equivalent to an acetaldehyde conversion amount which is the same as the total amount of propionic acid, crotonaldehyde, 2-ethylcrotonaldehyde, and hexyl iodide which are generated in a steady continuous reaction state. Actually, because propionic acid is the most in terms of quantity and accounts for the majority, the acetaldehyde amount almost corresponding to a molar amount of propionic acid can be withdrawn. That is, acetaldehyde can be withdrawn from a process liquid not only to reduce organic iodides and carbonyl impurities originating in acetaldehyde contained in product acetic acid but also to reduce the propionic acid content as well, which provides the advantage that acetic acid is easily refined.

According to the method in the present invention described above, a trace impurity concentration in a product can be reduced by reducing an acetaldehyde concentration in a reaction liquid.

However, when stricter quality is required, an acetaldehyde concentration in a reaction liquid has to markedly be reduced, which in turn requires the expansion of facilities such as a distillation column, an extraction column and a reactor. Accordingly, a large amount of investment in plants and equipment is required.

Thus, in the case described above, it is preferred that the method of the present invention and, for example, the method of treating acetic acid obtained by Macro-reticulated strong-acid cation exchange resin partially converted to the silver form (U.S. Pat. No. 4615806) are both used.

That is, liquid acetic acid obtained by maintaining the acetaldehyde concentration in the carbonylation reaction liquid at 400 ppm or less are contacted with strong acid cation exchange resins in which at least 1% of the active sites is substituted with silver and/or mercury forms. The liquid to be contacted with the strong acid cation exchange resins may be any liquid as long as it contains acetic acid as principal components. A process liquid having as low a methyl iodide concentration as possible is preferably used in order to protect the resins. In the present invention, acetic acid obtained via the line 17 passing through known processes such as distillation, are contacted with the specific strong acid cation exchange resins described above with obtain high purity acetic acid without employing any after-steps such as distillation. Or, they may be contacted to the specific strong acid cation exchange resins before passing through known processes such as distillation. Acetic acid coming out through the line 17 may be subjected to an operation such as distillation according to necessity after contact with to the strong acid cation exchange resins.

The strong acid cation exchange resins described above used for removing impurities such as iodides and the like are of a non-gel type and have active sites at least 1% of which is substituted with silver and/or mercury forms. An ion exchange membrane having active sites, at least 1% of which is substituted with silver and/or mercury forms, an ion exchange fiber, and polymer resins having functional groups forming coordinate complexes with silver and mercury, such as a polyvinylpyridine resin, can be used as well in place of the ion exchange resins described above.

With respect to the amounts of silver and/or mercury bonded to the resins, at least 1% of the active sites can be converted to the silver and/or mercury forms, and about 1% to 100% of the active sites can be converted to the silver and/or mercury Forms. About 25 to about 75% can preferably be converted to the silver and/or mercury forms.

The temperatures at which strong acid cation exchange resins like this are contacted with acetic acid are not specifically limited, and they can be contacted at every temperature extending widely from almost freezing points of liquid acetic acid to the decomposition temperatures of the resins. The temperature in practical use is usually about 17° to about 100° C., preferably 17° to 80° C.

Further, in addition to contacting with strong acid cation exchange resins, liquid acetic acid obtained by maintaining the acetaldehyde concentration in the carbonylation reaction liquid at 400 ppm or oxidation treatment such as ozonation, alkaline metal salt treatment or silver compound processing may be applied according to necessity. When these treatments are carried out, though the order of the respective treatment is not critical, the oxidation treatment is preferably carried out after the treatment of contacting with the cation exchange resins in order to prevent the cation exchange resins from being irreversibly swollen.

Higher quality acetic acid, which previously has been uneconomical by any possibility to be achieved through the removal of acetaldehyde, can be achieved by combining the removal of acetaldehyde from the system with treatment by contact with the specific cation exchange resins. In addition, the amount of the ion exchange resins required for obtaining acetic acid having sufficiently satisfactory quality can be minimized. In other words, the ion exchange resin amounts which have so far been used can be used longer in the present process than in the past.

EXAMPLE

Examples will be shown below to specifically explain the process of the present invention, but the present invention will not be limited by these examples. Parts shown in the examples mean weight parts unless otherwise described.

In the following examples, while test equipment for producing acetic acid shown in FIG. 1 was operated with a reaction liquid having the composition: methyl iodide of 14 weight %, water of 8 weight %, methyl acetate of 1.6 weight %, acetic acid of 70.9 weight %, lithium iodide of 5 weight %, and rhodium of 400 ppm, a part of the lower phase liquid 30 in the separator bath obtained after condensing the overhead 20 withdrawn from the methyl iodide-acetic acid splitter column was distilled in a distillation column of 80 plates in the following conditions to obtain an acetaldehyde concentrate from the top, and carbonyl impurities were removed from this concentrate.

| Composition of charged liquid: | |
| --- | --- |
| Methyl iodide | 89.4 weight % |
| Methyl acetate | 5.0 weight % |
| Acetic acid | 5.0 weight % |
| Water | 0.5 weight % |
| Acetaldehyde | 0.07 weight % |
| Paraldehyde | 0 weight % |
| Alkanes | 0.01 weight % |
| Others | 0.02 weight % |
| Distillation condition: | |
| Reflux ratio | 170 |
| Charged amount | 100 parts (285 kg/hr) |
| Withdrawn amount | 0.19 part from top, 99.81 parts from bottom |
| Charging plate | 70th plate from top |
| Top temperature | 54° C. |
| Bottom temperature | 82° C. |
| Top withdrawn liquid composition: | |
| Methyl iodide | 68.3 weight % |
| Methyl acetate | 0 weight % |
| Acetic acid | 0 weight % |
| Water | 0.7 weight % |
| Acetaldehyde | 29.0 weight % |
| Paraldehyde | 0.1 weight % |
| Alkanes | 1 weight % |
| Others | 0.9 weight % |

Removal of this top withdrawn liquid from the system makes it possible to control the acetaldehyde concentration in the reactor but because the methyl iodide concentration is high, there is a problem of the loss thereof or an environmental problem caused by the disposal thereof, and usually it is not preferable. Accordingly, a water extraction operation was carried out as shown in the following examples to obtain high purity acetic acid.

Example 1

It will be shown in the present example that the top withdrawn liquid from the 80 plate distillation column described above is used to carry out water extraction and that the extract thus obtained can be distilled to separate acetaldehyde. Extraction was carried out with a ratio S/F of water which was a solvent to the top withdrawn liquid from the 80 plates distillation column described above being set to 1 (weight ratio) and a theoretical plate of two plates. The extractability of acetaldehyde was 98%. Acetaldehyde of 154 g/hr could be removed by processing the whole amount of 540 g/hr of the top withdrawn liquid from the 80 plates distillation column described above. This could lead to removal of 57% of the amount of 270 g/hr of forming acetaldehyde in the reactor. A raffinate (methyl iodide-rich liquid) which had been refined by removing acetaldehyde was recirculated into the tenth plate from the top of the above 80 plate distillation column to thereby recirculate it into the reactor as a bottom withdrawn liquid from the above 80 plates distillation column. An extract (aqueous phase stream) with which acetaldehyde had been extracted was supplied to the subsequent distillation column, wherein acetaldehyde was withdrawn as a distillate, and water was withdrawn as a bottom product. In this distillation, separation could sufficiently be made at a theoretical plate of 8 plates and a reflux ratio of 0.3. With respect to operating pressure, any pressure can be used, and the operating pressure is not essential in this process. Water withdrawn from the bottom was recirculated to the extractor as a solvent. The acetaldehyde concentration in the reactor was 200 ppm. As a result thereof, the permanganate time of product acetic acid obtained was 200 minutes. A wet product stream withdrawn from the vicinity of the bottom of the methyl iodide—acetic acid splitter column 14 was dried by distillation. The concentrations of hexyl iodide and propionic acid in this dried product liquid were 9 ppb and 270 ppm, respectively.

There are shown extraction materials (top withdrawn liquid), extracts, raffinates, distillates, and bottom products in Table 1, the compositions of the lower phase liquid 30 in the separator and the composition of the recirculating liquid to the reactor in Table 2, and the composition of the reaction liquid in Table 3, respectively.

TABLE 3

|  | Reaction liquid composition |
| --- | --- |
| Acetaldehyde | 200 ppm |
| Methyl iodide | 14 weight % |
| Water | 8 weight % |
| Methyl acetate | 1.6 weight % |
| Hydrogen iodide | 0.5 weight % |
| Acetic acid | 70.9 weight % |
| Lithium iodide | 5 weight % |
| Rhodium | 400 ppm |

Example 2

A water-extracted processing amount of the acetaldehyde concentrate obtained from the lower phase liquid 30 in the liquid separator was changed in the same manner as that in Example 1 to change the acetaldehyde amount which was removed from the system as shown in Table 4. A non-processed acetaldehyde concentrate was recirculated into the reactor as a process liquid. This allowed the acetaldehyde concentration in the reaction liquid to be controlled as shown in Table 4 without changing the main composition in the reaction liquid. The concentrations of trace impurities contained in the dehydrated product acetic acid versus the acetaldehyde concentrations in the reaction liquid, and the permanganate time of product acetic acid obtained by further distilling dehydrated product acetic acid for removing high boiling matters are shown in Table 4.

TABLE 1

| | Composition (weight %) | | | | |
| --- | --- | --- | --- | --- | --- |
| | Extraction material | Extract | Raffinate | Distillate | Bottom liquid |
| Methyl iodide | 68.3 | 1.0 | 97.0 | 4.2 | 0 |
| Formic acid | 0 | 0 | 0 | 0 | 0.2 |
| Water | 0.7 | 76.8 | 0.2 | 2.4 | 99.8 |
| Acetaldehyde | 29.0 | 21.8 | 0.8 | 91.4 | 0 |
| Paraldehyde | 0.1 | 0 | 0.1 | 0 | 0 |
| Alkanes | 1.0 | 0 | 1.5 | 0 | 0 |
| Others | 0.9 | 0.5 | 0.4 | 2.0 | 0 |

TABLE 2

| | Composition (weight %) | |
| --- | --- | --- |
| | Lower phase liquid in liquid separator | Recirculating liquid to reactor |
| Methyl iodide | 89.4 | 89.4 |
| Methyl acetate | 5.0 | 5.0 |
| Acetic acid | 5.0 | 5.0 |
| Water | 0.5 | 0.5 |
| Acetaldehyde | 0.07 | 0.016 |
| Paraldehyde | 0 | 0 |
| Alkanes | 0.01 | 0.01 |
| Others | 0.02 | 0.0 |

TABLE 4

| Removed AD amount (g/hr) | Reaction liquid AD concentration (ppm) | Dehydrated product acetic acid | | | | Permanganate time of product acetic acid (minute) | Remark |
|---|---|---|---|---|---|---|---|
| | | HexI (ppb) | CR (ppm) | ECR (ppm) | BA (ppm) | PA (ppm) | |
| 13 | 800 | 100 | 4 | 5 | 17 | 620 | 40 | Comparative |
| 50 | 500 | 50 | 2.5 | 1.6 | 8.5 | 520 | 85 | Example |
| 131 | 300 | 13 | 1.4 | 0.4 | 3.7 | 330 | 140 | Invention |
| 140 | 250 | 11 | 1.1 | 0.3 | 3.1 | 310 | 180 | Example |
| 154 | 200 | 9 | 0.8 | 0.1 | 2.0 | 270 | 200 | |

AD—Acetaldehyde
HeXI—Hexyl iodide
CR—Crotonaldehyde
ECR—2-Ethylcrotonaldehyde
BA—Butyl acetate
PA—Propionic acid As shown in Table 4, it can be found that the concentrations of crotonaldehyde, 2-ethylcrotonaidehyde, butyl acetate, and propionic acid, as well as hexyl iodide, are rapidly reduced and the permanganate time is increased to a large extent by setting the acetaldehyde concentration in the reaction liquid to 400 ppm or less.

Example 3

It will be shown in the present example that acetaldehyde can be extracted with water at theoretical stages of one stage and two stages, even if the acetaldehyde concentrations are low.

A liquid obtained by diluting the top withdrawn liquid from the 80 stage distillation column with methyl iodide was used. Extraction, which was carried out at an S/F weight ratio of 0.5 and a theoretical stage of one stage, resulted in obtaining an acetaldehyde extractability of 68%. Extraction, which was carried out at a theoretical stage of two stages, resulted in obtaining an acetaldehyde extractability of 95%.

These results are shown in Table 5.

generate paraldehyde and metaldehyde, that is, a top temperature of 56° C., a reflux tank temperature of 32° C., and a top pressure of 2.5 kg/cm² G. The distillation column 60 was a packed column having a theoretical stage of 8 stages, and the total amount of the top distillate from the distillation column 40 was charged into the fourth stage from the top. The reflux ratio was 40, and the bottom temperature was 74° C.

Regulating a charged amount to the distillation column of 60 to 100 parts, 38.5 parts of an acetaldehyde concentrate (acetaldehyde concentration: 88.1 wt %) was separated and removed from the top, and 61.5 parts of a liquid rich in methyl iodide (methyl iodide: 82.8 wt %) were withdrawn from the bottom as a bottom product, which was recirculated into the distillation column 40. The concentration of hexyl iodide contained in the product acetic acid was 28 ppb.

The composition of the reaction liquid is shown in Table 6, the compositions of the charged liquid to the distillation column 40 and the top withdrawn liquid from the distillation column 40 are shown in Table 7, and the compositions of the charged liquid to the distillation column 60, the distillate from the distillation column 60, and the bottom products are shown in Table 8, respectively.

TABLE 5

| | Composition of extraction material | Composition at theoretical stage of one stage (weight %) | | Composition at theoretical stage of two stages (weight %) | |
|---|---|---|---|---|---|
| | (weight %) | Extract | Raffinate | Extract | Raffinate |
| Methyl iodide | 85.5 | 0.9 | 91.9 | 1.1 | 96.3 |
| Water | 0.2 | 85.5 | 0.1 | 73.6 | 0.2 |
| Acetaldehyde | 9.3 | 10.2 | 2.9 | 21.3 | 1.2 |
| Others | 5.0 | 3.4 | 5.1 | 4.0 | 2.3 |

Example 4

While operating the test equipment for producing acetic acid shown in FIG. 1 and 2, the lower phase liquid 30 in the liquid separator obtained after condensing the overhead 20 from the methyl iodide-acetic acid splitter column 14 was introduced into the seventieth stage from the top of the distillation column 40 having the total of 80 stages (Sieve Tray) and distilled under the conditions of a reflux ratio of 270, a top temperature of 54° C., and a bottom temperature of 82° C. Setting a charged amount to 100 parts, 0.33 part was withdrawn from the top, and 99.67 parts from the bottom. For reasons of facilities, a top distillate from the distillation column 40 was charged into the second distillation column 60 and distilled under a condition which did not

TABLE 6

| Reaction liquid | Composition (wt %) |
|---|---|
| Acetic acid | 70.9 |
| Methyl iodide | 14.0 |
| Water | 8.0 |
| Methyl acetate | 1.6 |
| Rhodium | 400 ppm* |
| Lithium iodide | 5.0 |
| Acetaldehyde | 345 ppm* |

*Unit: ppm

TABLE 7

| | Composition (wt %) | |
|---|---|---|
| | Charged liquid | Top withdrawn liquid* |
| Methyl iodide | 89.2 | 53.4 |
| Methyl acetate | 5.0 | 0.1 |
| Acetic acid | 5.0 | 0 |
| Water | 0.5 | 0.5 |
| Acetaldehyde | 0.12 | 40.1 |
| Paraldehyde | 0 | 0.6 |
| Metaldehyde | 0 | 0 |
| Alkanes | 0.01 | 0.2 |
| Others | 0.2 | 5.1 |

*Distillate

TABLE 8

| | Composition (wt %) | | |
|---|---|---|---|
| | Charged liquid | Distillate | Bottom liquid |
| Methyl iodide | 53.4 | 6.3 | 82.8 |
| Methyl acetate | 0.1 | 0 | 0.2 |
| Water | 0.5 | 0 | 0.8 |
| Acetaldehyde | 40.1 | 88.1 | 11.1 |
| Paraldehyde | 0.6 | 0 | 0 |
| Metaldehyde | 0 | 0 | 0 |
| Alkanes | 0.2 | 0.5 | 0.02 |
| Others | 5.1 | 5.1 | 5.1 |

Comparative Example 2

The overhead 20 withdrawn from the methyl iodide—acetic acid splitter column was circulated into the reactor as it was without distilling. As a result thereof, the concentration of acetaldehyde in the reactor was 800 ppm, acetaldehyde was not separated and removed, and the concentration of hexyl iodide contained in product acetic acid was 100 ppb. Also, a wet product stream withdrawn from the vicinity of the bottom of the methyl iodide-acetic acid splitter column was dried by distillation, and the concentration of propionic acid contained in this dried product liquid was 620 ppm.

Example 5

The top withdrawn liquid from the distillation column 40 in Example 1 was introduced into the distillation column 60 and distilled under conditions which generate paraldehyde and metaldehyde, that is, a. top temperature of 28.7° C. and a reflux tank temperature of −10° C. The other conditions in the distillation column 60 were a reflux ratio of 15, a bottom temperature of 64.6° C. and a top pressure of 1.033 kg/cm² in an oldershaw having 20 total stages. Further, methanol of 100 parts was introduced into the seventeenth stage from the top of the distillation column 60. The top liquid of 100 parts withdrawn from the distillation column 40 was introduced into the distillation column 60, and 74 parts was withdrawn from the top, which was recirculated into the top of the distillation column 40. The remaining 26 parts was separated and removed as a bottom liquid. Methanol was charged to prevent a nozzle at the lower part of the distillation column from being clogged and enable the bottom liquid to be withdrawn.

The concentration of hexyl iodide contained the product acetic acid was 40 ppb.

Further, the concentration of acetaldehyde in the reactor was 400 ppm.

The composition of the charged liquid to the distillation column 60, the distillate from the distillation column 60 and the bottom liquid are shown in Table 9.

TABLE 9

| | Composition (wt %) | | | |
|---|---|---|---|---|
| | Charged liquid | | | |
| | From 67 | From 44 | Distillate | Bottom liquid |
| Methyl iodide | | 53.4 | 69.1 | 1.8 |
| Methyl acetate | | 0.1 | 0.06 | 0.06 |
| Water | | 0.5 | 0 | 0.4 |
| Acetaldehyde | | 40.1 | 22.4 | 5.1 |
| Paraldehyde | | 0.6 | 0.02 | 0.7 |
| Metaldehyde | | 0 | 0 | 13.4 |
| Alkane | | 0.2 | 0.2 | 0 |
| Others | | 5.1 | 6.9 | 0 |
| Methanol | 100 | | 1.5 | 78.5 |

Comparative Example 3

The same procedure as that in Example 5 was repeated, except that a methanol solution was not charged. The result was that the deposition of metaldehyde crystal clogged the nozzle at the lower part of the distillation column and prevented operation.

Example 6

Conventional separating operations, that is, dehydrating and distillation operation for removing high boiling matters were applied to the crude acetic acid liquid obtained in Example 1 (obtained from the distillation column in FIG. 1 via the line 17) to find that crotonaldehyde of 0.8 ppm, 2-ethylcrotonaidehyde of 0.1 ppm and hexyl iodide of 9 ppb were contained in the acetic acid.

This crude acetic acid was passed through the ion exchange resin column at the temperature of 30° to 40° C. The ion exchange resins used here were obtained by exchanging 50% of the active sites of RCP 160M (macroporous strong acid cation exchange resin, manufactured by Mitsubishi Chemicals Co., Ltd.) with silver. Crotonaldehyde of 0.8 ppm and 2-ethylcrotonaidehyde of 0.1 ppm were contained in product acetic acid obtained after ion exchange processing. Hexyl iodide was contained at 4 ppb or less. A resin amount required for maintaining this product quality for one year was an amount corresponding to SV=60 (Hr$^{-1}$) in terms of SV.

Example 7

Crude acetic acid obtained in the above Example 6 after removing high boiling matters was passed through the ion exchange resin column at the temperature of 30° to 40° C. The ion exchange resins used here were obtained by exchanging 42% of the active sites of Amberlist 15 (macroporous strong acid cation exchange resin, manufactured by Rohm & Haas Co., Ltd.) with silver. Crotonaldehyde of 0.8 ppm and 2-ethylcrotonaldehyde of 0.1 ppm were contained in the product acetic acid obtained after ion exchange processing. Hexyl iodide was contained at 4 ppb or less. A resin amount required for maintaining this product quality for one year was an amount corresponding to SV=80 (Hr$^{-1}$) in terms of SV.

Example 8

Crude acetic acid obtained in the above Example 6 after removing high boiling matters was passed through the ion exchange resin column at a temperature of 70° to 80° C. and a SV=60 (Hr$^{-1}$). The ion exchange resins used here were obtained by exchanging 50% of the active sites of RCP 160M (macroporous strong acia cation exchange resin, manufactured by Mitsubishi Chemicals Co., Ltd.) with silver. Crotonaldehyde of 0.8 ppm and 2-ethylcrotonaldehyde of 0.1 ppm were contained in product acetic acid obtained after ion exchange processing. Hexyl iodide was contained in 4 ppb or less. The ion exchange processing could be continued in this condition while maintaining the product quality described above for 2 years.

Example 9

Crude acetic acid obtained in the above Example 6 after removing high boiling maters was passed through the ion exchange resin column at a temperature of 70° to 80° C. and a SV=80 (Hr$^{-1}$). The ion exchange resins used here were obtained by exchanging 42% of the active sites of Amberlist 15 (macroporous strong acid cation exchange resin, manufactured by Rohm & Haas Co., Ltd.) with silver. Crotonaldehyde of 0.8 ppm and 2-ethylcrotonaldehyde of 0.1 ppm were contained in product acetic acid obtained after ion exchange processing. Hexyl iodide was contained at 4 ppb or less. The ion exchange processing could be continued in this condition while maintaining the product quality described above for 2 years.

What we claim is:

1. A process for producing a high purity acetic acid, comprising the steps of continuously reacting methanol with carbon monoxide in the presence of a rhodium catalyst, an iodide salt, and methyl iodide, wherein the reaction is carried out while maintaining an acetaldehyde concentration in the reaction liquid at 400 ppm or lower.

2. The process as described in claim 1, wherein the reaction is carried out by removing acetaldehyde from a process liquid being circulated into a reactor to maintain the acetaldehyde concentration in the reaction liquid at 400 ppm or lower.

* * * * *